US011270576B2

(12) United States Patent
Franz et al.

(10) Patent No.: US 11,270,576 B2
(45) Date of Patent: Mar. 8, 2022

(54) SYSTEM AND PROCESS FOR THE AUTOMATIC DETECTION OF HAZARDOUS SITUATIONS

(71) Applicant: Drägerwerk AG & Co. KGaA, Lübeck (DE)

(72) Inventors: Frank Franz, Lübeck (DE); Stefan Schlichting, Lübeck (DE); Jasper Diesel, Lübeck (DE)

(73) Assignee: Drägerwerk AG & Co. KGaA, Lübeck (DE)

(*) Notice: Subject to any disclaimer, the term of this patent is extended or adjusted under 35 U.S.C. 154(b) by 2 days.

(21) Appl. No.: 16/890,714

(22) Filed: Jun. 2, 2020

(65) Prior Publication Data

US 2020/0388148 A1 Dec. 10, 2020

(30) Foreign Application Priority Data

Jun. 7, 2019 (DE) .................. 10 2019 003 999.8

(51) Int. Cl.
*G08B 29/18* (2006.01)
*G06K 9/00* (2006.01)
*G08B 21/04* (2006.01)

(52) U.S. Cl.
CPC ....... *G08B 29/185* (2013.01); *G06K 9/00201* (2013.01); *G08B 21/0469* (2013.01)

(58) Field of Classification Search
None
See application file for complete search history.

(56) References Cited

U.S. PATENT DOCUMENTS

| 10,043,360 | B1* | 8/2018 | Mullins | G08B 13/19652 |
| 10,090,068 | B2* | 10/2018 | Kusens | G16H 40/20 |
| 10,524,722 | B2* | 1/2020 | Kusens | A61B 5/447 |
| 10,984,282 | B2* | 4/2021 | Hacker | G06Q 10/087 |
| 2012/0075464 | A1* | 3/2012 | Derenne | A61B 5/0013 348/135 |
| 2013/0216094 | A1* | 8/2013 | DeLean | G06K 9/00335 382/103 |
| 2017/0193279 | A1* | 7/2017 | Kusens | A61B 5/0077 |
| 2019/0205630 | A1* | 7/2019 | Kusens | A61B 5/1113 |
| 2019/0206218 | A1* | 7/2019 | Kusens | H04N 13/204 |
| 2020/0202177 | A1* | 6/2020 | Buibas | G06N 20/00 |

FOREIGN PATENT DOCUMENTS

DE 102013017264 A1 4/2015

* cited by examiner

*Primary Examiner* — Fekadeselassie Girma
(74) *Attorney, Agent, or Firm* — McGlew and Tuttle, P.C.

(57) ABSTRACT

A system (100) detects hazardous situations in a medical setting. A sensor unit (110) has optical sensors (112) to determine a sensor signal (114), and to output same in real time, which includes sensor data indicating a sequence of three-dimensional views of a monitored area (102) over a monitoring time. A processor unit (12) identifies a number of objects (122) to be protected based on the three-dimensional views, detects hazardous objects (124) based on the three-dimensional views, determines a number of object pairs (105), monitors positions of the protected objects and hazardous objects of the object pair over the monitoring time, assigns hazard values to the object pairs, calculates current hazard values for object pairs up to a current time over an analysis time interval and outputs a corresponding alarm signal (126) if a calculated hazard exceeds a threshold value. An output unit (130) triggers an alarm.

20 Claims, 5 Drawing Sheets

SYSTEM AND PROCESS FOR THE AUTOMATIC DETECTION OF HAZARDOUS SITUATIONS

CROSS REFERENCE TO RELATED APPLICATIONS

This application claims the benefit of priority under 35 U.S.C. § 119 of German Application 10 2019 003 999.8, filed Jun. 7, 2019, the entire contents of which are incorporated herein by reference.

TECHNICAL FIELD

The present invention pertains to a system and to a process for the automatic detection of hazardous situations within a monitored area for objects in a medical setting. The present invention pertains, furthermore, to a program with a program code for carrying out the process according to the present invention.

TECHNICAL BACKGROUND

It is a known problem in medical settings that confused patients jeopardize their own treatment, for example, by removing dressings, pulling out catheters or interacting with complicated medical devices themselves. In order to prevent such activities of the patient in his own interest in time, it is known that a camera-based monitoring system is provided to monitor beds within a hospital.

U.S. Pat. No. 10,090,068 describes a process by which a monitoring is carried out in a clinical setting to determine whether a hand of a patient enters into a predefined zone within a monitored area for a predefined minimum duration. The predefined zone may be located, for example, in the area of a catheter or in the area of a wound of the patient. The process described makes it possible hereby to detect the entry of the hand of the patient into an area that is hazardous for him.

SUMMARY

An object of the present invention is to make possible an improved automatic detection of hazardous situations for objects in a medical setting, especially an improved avoidance of the outputting of false alarms and especially an early detection of relevant hazardous situations.

A system for the automatic detection of hazardous situations within a monitored area for objects in the medical setting with a sensor unit, with a processor unit and with an output unit is proposed according to the present invention to accomplish this object.

The sensor unit has a number of optical sensors and is configured to determine a sensor signal and to output it in real time. The number of optical sensors can, furthermore, be arranged in the medical setting and be configured such that the sensor signal comprises sensor data that indicate a sequence of three-dimensional views of the monitored area over a monitoring time.

The processor unit is configured to receive the sensor signal and to carry out the identification of a number of objects to be protected within the monitored area on the basis of the indicated three-dimensional views. Furthermore, the processor unit is configured to carry out on the basis of the indicated three-dimensional views a detection, especially an automated detection, of hazardous objects within the monitored area and to determine a number of object pairs by assigning an object to be protected from the number of objects to be protected and a hazardous object. Furthermore, the processor unit is configured to monitor in the course of the monitoring time the positions of an object to be protected and a hazardous object of a respective object pair within the monitored area and to assign a current hazard value to a respective object pair as a function of the two current positions and of a group of parameters arising from an analysis of earlier analysis data. And finally, the processor unit is further configured to calculate the respective current hazard values up to the current time over an analysis time interval, especially over a predefined analysis time interval, for each object pair and to output a corresponding alarm signal if a hazard parameter of an object pair, which was thus calculated, exceeds a predefined threshold value.

The output unit is configured to receive the alarm signal and to trigger an alarm as a function of the alarm signal.

It was discovered within the framework of the present invention that a current situation within the monitored area must be analyzed qualitatively in order to avoid false alarms and in order to ensure an especially early detection of hazards. Objects to be protected are identified and hazardous objects within the monitored area are detected for this purpose according to the present invention. Furthermore, the system according to the present invention also takes parameters arising from earlier analysis data into consideration for such a qualitative analysis, in addition to current data.

A contact between an object to be protected and a hazardous object is considered as a hazardous situation to be avoided within the framework of the present invention, because such a contact may have disadvantageous consequences for the health of the patient in routine medical practice, for example, due to incorrect operation of a medical device or due to a tube or a catheter being pulled out by the patient.

It is advantageously ensured by the system according to the present invention that hazardous situations can rapidly be detected within the monitored area. In particular, it is not necessary to wait until a hazardous situation develops, for example, due to the entry of a hand of the patient into the area at risk, for example, in the proximity of a catheter. By monitoring the two current positions combined with the analysis of earlier analysis data, an especially meaningful hazard value is thus determined in time, from which the hazard parameter of a respective object pair, which value characterizes the current hazard, is obtained.

By using a predefined threshold value, it is advantageously possible to predefine in a user-specific manner a probability starting from which there could be a hazard that a corresponding alarm signal is outputted. If the threshold value is predefined such that the alarm signal is already outputted at a low probability of a hazard, this would, in turn, lead to a higher number of false alarms than when the alarm signal is outputted only in case of a moderate probability of a hazard.

The identification of the number of objects to be protected may be carried out, for example, in an automated manner, manually or by gesture control.

The detection of hazardous objects is carried out especially preferably in an automated manner. Such an automated detection advantageously makes possible a rapid detection of these objects, because it is not necessary to wait for a manual entry. Furthermore, this makes possible the detection of hazardous objects to which a user of the system would not possibly have assigned any hazard potential. This automated detection is preferably carried out by carrying out an algorithm for object detection, by which the monitored area is searched for predefined objects. Such algorithms are well known and will not therefore be explained in detail below. The automated detection may also be carried out on the basis of properties of objects, for example, a detected velocity of an object or a movement direction of an object. In particular, the automated detection may be based on an analysis of the sequence of three-dimensional data. As an alternative or in addition, the hazardous objects may be detected manually or by gesture control and identified thereby for the processor unit.

According to the present invention, the sensor data may be data indicating a two-dimensional arrangement, which make it possible to determine a three-dimensional view of the monitored area. The sequence of three-dimensional views according to the present invention is obtained from a chronological sequence of individual sensor data to yield the sensor signal outputted in real time. Three-dimensional views may also be three-dimensional point clouds according to the present invention. These make possible a greatly reduced storage and transmission effort compared to the transmission of complete images. Furthermore, the use of three-dimensional point clouds makes possible an especially simple combination of data of a plurality of optical sensors into a three-dimensional view. The use of three-dimensional point clouds makes, furthermore, possible an especially simple determination of a distance between objects by a determination of the distance of the corresponding points from the point cloud. In particular, the three-dimensional point cloud can be reduced by an automated prefiltering to relevant parts of the monitored area, for example, on the basis of detected brightness contrasts, so that large monochrome and planar areas, for example, a floor, can be removed from the determined sensor data.

The detailed structure of a sensor unit according to the present invention with a number of optical sensors for providing a sequence of three-dimensional views is known and such sensor units are already commercially available, so that the mode of operation of this sensor unit and of the at least one optical sensor from the number of optical sensors will not be explained in detail below.

The earlier analysis data comprise data that were detected at an earlier time preceding the current time and are suitable for an analysis of the current hazardous situation. In particular, the earlier analysis data may be based on earlier positions of the object to be protected and of the hazardous object of a respective object pair relative to one another.

An alarm is defined within the framework of the present invention as an output of a piece of information, which informs the recipient of the output about the presence of a state of alarm. An alarm may comprise an optical and/or acoustic output and/or a logging of the state of alarm in this sense. The triggering according to the present invention of an alarm may also comprise in this sense the outputting of a piece of alarm information corresponding to the alarm signal, by which a recipient of the output can be informed about the presence of a state of alarm.

The area monitored for objects in the medical setting is, for example, an area intended for patients in a hospital ward. In another example, this area is an area intended for treated persons within a room intended for assisted living.

Preferred embodiments of the system according to the present invention will be described below.

In a preferred embodiment, the assignment between an object to be protected and a hazardous object depends on a current position of the hazardous object within the monitored area relative to the object to the protected. Having to monitor a needlessly large number of object pairs by the system according to the present invention is avoided hereby. An object known basically as a hazardous object, for example, a hand, is thus usually only hazardous if this object is located in the vicinity of an object to be protected or is moving towards the object to be protected. Furthermore, the assignment according to this embodiment makes it possible to form object pairs in which different objects to be protected are assigned to respective different hazardous objects to form object pairs. This makes allowance for the circumstance that a hazardous object, which is located in the vicinity of a first object to be protected, may represent a serious risk to this object, while it may not currently possibly represent any risk to a second object to be protected, which is located at a great distance and no corresponding object pair needs to be monitored.

In an especially preferred embodiment, the parameters obtained from an analysis of earlier analysis data, especially earlier positions, represent at least a distance between the objects of an object pair and a direction of a movement of the objects of an object pair relative to one another. A future distance between an object to be protected and a hazardous object within an object pair in relation to one another can be inferred especially advantageously in this embodiment. Thus, a velocity of the objects in question can be inferred from a change in the distance between the objects. In a preferred variant, a higher current hazard value is obtained for a positive velocity at which the objects are moving towards one another than for a lower velocity. In another variant of the embodiment, the current hazard value is formed in such a manner than when the object to be protected and the hazardous object are moving away from one another, the hazard parameter of this object pair is stagnant or decreases compared to an earlier hazard parameter. The direction of the movement is preferably determined by an analysis of the change in the distance in the course of the past detected positions. In a variant of this embodiment, a distance of the geometric centers of the two object of an object pair is determined as a distance. In an alternative variant of this embodiment, a distance of the points representing a respective object of the object pair, which points are located closest to one another, is determined as the distance. In another variant of this embodiment, a contact time, at which a contact would develop between the two objects of an object pair during constant movement, is calculated by the processor unit from the distance and the movement direction of the two objects of an object pair. The contact time additionally forms in this variant a parameter obtained from the analysis of earlier analysis data. The calculation of the contact time is especially advantageous when one of the objects is occasionally hidden for the sensor unit, for example, when the hazardous object is located behind another object, e.g., under a ceiling. In view of a currently calculated contact time, which represents a prediction for a duration until a future hazardous situation, an alarm signal can nevertheless be outputted in time and a corresponding alarm can be triggered during such an occasional coverage of the hazardous object or of the object to be protected.

In an especially advantageous embodiment, an importance value, which is obtained from a predefined relevance level of the object to be protected and/or from a predefined hazard level of the hazardous object, and wherein the current hazard value of the object pair depends on the importance value, is assigned to each object pair by the processor unit. The circumstance that certain object pairs may lead to a very great hazard to the health of the patient, whereas other object pairs entail only a slight hazard can be taken into consideration by such an importance value. For example, an especially high relevance level can thus be assigned to a wound that is currently to be healed as an object to be protected, so that any hazard to this wound and to the corresponding healing process leads rapidly to high hazard values and hence to a high hazard parameter and to a prompt alarm generation by the alarm signal. Furthermore, a higher hazard level can be assigned to a hand as a hazardous object than to a head, so that a higher importance value is assigned basically to each object pair including the hand because a corresponding interaction with an object to be protected represents an especially great hazard to the health of the patient. The assignment of hazard level and relevance level is carried out at least partially manually in a preferred embodiment. In an alternative or additional embodiment, the assignment of hazard level and relevance level is carried out by a predefined assignment to predefined objects, which assignment is stored in a memory of the processor unit. The determination of the importance value from the relevance level and hazard level is obtained, for example, from a sum of the two levels, from a product of the two levels, from a mean value of the two levels, from a maximum value of the two levels and/or from another suitable algebraic assignment rule. In an alternative variant, the importance value is obtained directly from the relevance level or directly from the hazard level.

In an embodiment that is an alternative to the previous embodiment, the importance value is obtained from an assignment of the importance value to the predefined object pair, which assignment is stored in a memory.

In another advantageous embodiment, the current hazard value of an object pair also depends on whether a direct path between the object to be protected and the hazardous object is obstructed by an additional object. The circumstance that an obstruction of the path between the two objects of an object pair causes the risk of a contact of the two objects to be very low at least for a certain time period is advantageously taken into consideration hereby. Correspondingly, the obstruction of the path preferably leads to a current hazard value that leads to a reduction of the hazard parameter determined.

In a preferred embodiment, the monitoring of an object pair by the processing unit is ended if the calculated hazard parameter drops below a lower threshold value. The lower threshold value is formed here such that there is no risk to the health of the patient from the originally hazardous object.

The identification of the number of objects to be protected and/or of the hazardous objects is carried out especially advantageously by an automated object detection. Processes for automated object detection are generally known, so that they will not be explained in detail below. Predefined objects can be detected especially reliably by known automated object detection algorithms. It is especially advantageous hereby to define common medical objects to be protected from the medical setting prior to the use of the system according to the present invention, for example, a tube, a catheter, a supply cable, dressings and/or medical devices. If the processor unit detects such an already defined object in the monitored area, it can be identified automatically as an object to be protected.

In another advantageous embodiment, the number of objects to be protected is identified at least partially by an interaction with a user of the system. In a preferred variant, the interaction with the user is a manual definition of the object to be protected, for example, by marking this object on a graphic user surface, especially by marking by clicking a mouse or by touch. In another advantageous variant, the interaction with the user is a gesture control, for example, by medical staff triggering the activation of the monitoring for an object defined by the gesture in the form of a predefined gesture within the monitored area. In another advantageous variant, the interaction is a predefined treatment action within the monitored area, so that, for example, a dressing is detected by the processor unit as an object to be protected by said dressing being applied, or a tube is detected as an object to be protected by the fact that it is used during the integration into a patient. All variants of this embodiment have the advantage that even unusual shapes and types of objects to be protected, which cannot possibly be detected by an automatic object detection, can be identified as objects to be protected by the user. Furthermore, it can be ensured by the user in this embodiment that no object to be protected is overlooked by the processor unit, which is especially advantageous for the safety of the patient.

In an embodiment of the system according to the present invention, the analysis time interval is the time interval that is formed by a determination time for the determination of the corresponding object pair and the current time. All hazard values that were determined since the assignment of the objects to an object pair are advantageously taken into consideration in this embodiment. A future behavior of the objects of an object pair relative to one another can be inferred hereby over time in an especially trustworthy manner due to the especially accurate qualitative analysis.

In an advantageous embodiment, the system according to the present invention has, furthermore, a user interface, which is connected to the processor unit and which is configured to make possible a manual control of the identification of an object to be protected, of the detection of a hazardous object and/or of the assignment of the two objects to an object pair. Such a user interface may be embodied, for example, by a keyboard, by a touch display, by a computer mouse, by an optical sensor and/or by a joystick. The operation of the processor unit by the user interface according to this embodiment advantageously makes it possible to identify the object to be protected in an especially reliable manner and/or to detect the hazardous object in an especially reliable manner and/or to assign the two objects to an object pair in an especially reliable manner. In particular, errors that may occur during the automated identification, detection and/or assignment are avoided.

In an especially preferred embodiment, the object to be protected is at least one object from the group comprising a person, neck, extremity, infusion, medical device, cable, flexible tube, tube, dressing, and wound. Such objects regularly form objects to be protected in routine clinical practice, so that their manual and/or automatic identification as an object to be protected is especially advantageous. For example, the entire patient shall be defined as the person in this connection, so that an alarm generation is provided in this case in case of any contact with the patient, especially by unauthorized persons.

In an especially advantageous embodiment of the system according to the present invention, the sensor unit is further configured to output sensor data, which pertain to an identified object that is to be protected, less frequently within the framework of the sensor signal, to the processor unit, as sensor data, which pertain to a detected, currently hazardous object. The fact that the objects to be protected, for example, in a group of objects according to the above embodiment, are objects that do not typically perform any movement or do perform only a slow movement in the clinical setting is advantageously utilized in this embodiment. As a result, a data stream between the sensor unit and the processor unit and/or a storage location for received sensor data can be advantageously reduced hereby in this embodiment.

In another advantageous embodiment, the processor unit is configured to filter the received sensor signal and to use only the filtered signal for the further processing, especially for the further monitoring of object pairs. Only areas of the monitored area in which a movement or a change of the monitored area has taken place since the last time increment are preferably indicated here in the filtered signal.

In an especially preferred embodiment of the system according to the present invention, the hazardous object is at least one object from the group comprising the hand, foot, person, head, animal, and bed rail. Such objects can advantageously be detected especially reliably in an automated manner. Furthermore, said objects may lead in a clinical setting to an interaction with an object to be protected, which interaction usually represents a risk to the health of the patient.

In an especially advantageous embodiment, the alarm signal indicates the object to be protected and/or the hazardous object. In a variant of this embodiment, the triggered alarm indicates the objects to be protected and/or the hazardous object. As a result, a user of the system according to the present invention can detect the existing hazardous situation already on perceiving an alarm triggered by the alarm signal and possibly take actions to ensure the patient's health especially rapidly.

Different object pairs triggering the alarm signal may especially advantageously also lead to different types of alarm generation. For example, an alarm triggered by a stranger as a hazardous object may thus be indicated at least additionally in the security service of the corresponding hospital. In another example, an alarm triggered by a bed rail as a hazardous object is outputted as an alarm within the corresponding room only. In another example, an alarm triggered by an animal as a hazardous object is advantageously outputted within the entire corresponding hospital ward, because this animal could represent a hazard for other patients as well.

In another embodiment, the processor unit is configured to output an additional corresponding alarm signal if the alarm generation parameter of the object pair, which was thus calculated, exceeds another predefined threshold value, in which case the additional predefined threshold value is higher than the predefined threshold value. Different alarm stages can be triggered hereby corresponding to the hazard that is currently present for the health of the patient. For example, an alarm perceptible only locally in the hospital room is thus outputted when the predefined threshold value is reached and a global alarm also perceptible in an area in which medical staff is present is outputted when the additional predefined threshold value is reached.

In another embodiment according to the present invention, the alarm signal triggers a logging of the currently existing hazardous situation within a corresponding memory of the system according to the present invention. Adverse effects on the patient's health can advantageously be retrospectively reconstructed hereby based on an earlier hazardous situation.

In a preferred embodiment of the system according to the present invention, the alarm signal triggers an alarm corresponding to the object pair triggering the alarm signal at the object to be protected and/or at the hazardous object. In a variant of this embodiment, the alarm at the object to be protected leads to an adaptation of this object, which reduces the risk to the patient's health. For example, a medical device is adapted as an object to be protected in one variant such that it does not accept any accidental input by the user. In another example, an audio message is sent as an alarm to the person forming the hazardous object, so that this person is informed about the risk to the patient's health.

According to another aspect of the present invention, the above-mentioned object is accomplished by a process for the automatic detection of hazardous situations within a monitored area for objects in the medical setting.

The process according to the present invention has the following steps in this case:

Determination of a sensor signal, which comprises sensor data, which indicate a sequence of three-dimensional views of the monitored area over a monitoring time, and outputting of the sensor signal in real time, reception of the sensor signal, identification of a number of objects to be protected within the monitored area on the basis of the indicated three-dimensional views, detection, especially automatic detection, of hazardous objects within the monitored area on the basis of the indicated three-dimensional views, determination of a number of object pairs by an assignment between an object to be protected from the number of objects to be protected and a hazardous object, assignment of a current hazard value to a respective object pair as a function of the current positions of the object to be protected and of the hazardous object and of a group of parameters obtained from an analysis of earlier analysis data, calculation of the current hazard values for a respective object pair to form a respective hazard parameter over an analysis time interval until the current time, outputting of a corresponding alarm signal if the hazard parameter thus determined exceeds a predefined threshold value, and reception of the alarm signal and triggering of an alarm as a function of the alarm signal.

The process according to the present invention advantageously makes it possible to detect a hazardous situation especially rapidly while avoiding false alarms.

The calculation of the current hazard values for a respective object pair over the respective analysis time interval is especially advantageous, because a future development of the positions of a respective object pair can be inferred especially reliably by taking into consideration the more recent past of the monitored area.

Further, it is advantageous that the hazardous objects are preferably detected in an automated manner, because it can be ensured hereby that non-hazardous objects are overlooked during a, for example, manual entry of these objects.

In an especially preferred embodiment of the process according to the present invention, the calculation of the current hazard values comprises the addition of these current hazard values up to the current time to the respective hazard parameter of the object pair. The addition represents an especially simple mathematical operation, which makes possible an especially rapid processing by the processor unit by an especially rapid calculation of the current hazard values. The current hazard value may also be negative in a preferred variant of this embodiment, so that the added-up hazard parameter may also decrease again depending on the actions taken within the monitored area, for example, when the hazardous object and the object to be protected move again away from each other after initially approaching each other. A detailed description of how such a determination of the hazard parameter can be carried out can be found in the description of FIGS. 3 through 5.

In another embodiment of the process according to the present invention, this process is stopped if medical staff is detected by the processor unit within the monitored area. Such a detection may be carried out, for example, by reading an identification number carried by the medical staff. The process according to this embodiment is preferably continued together with the hitherto determined hazard values as soon as the medical staff has left the monitored area again.

Furthermore, the above-mentioned object is accomplished by a program with a program code for carrying out the process according to at least one of the above-mentioned embodiments of the process according to the present invention when the program code is run on a computer, on a processor or on a programmable hardware component.

The program may also carry out only a part of the data processing according to the present invention. At least the function of the processor unit and of the analysis unit are preferably controlled by a program and/or by consecutive parts of the program. In particular, the processing of the sensor data into the sensor signal is controlled by a separate part of the program within a processor of the sensor unit in embodiments according to the present invention of the program. The program according to the present invention is preferably carried out by a processor of the system according to the present invention. As an alternative, the program is carried out at least by a first processor of the processor unit and by a second processor of the output unit.

The present invention shall now be explained in more detail on the basis of advantageous exemplary embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
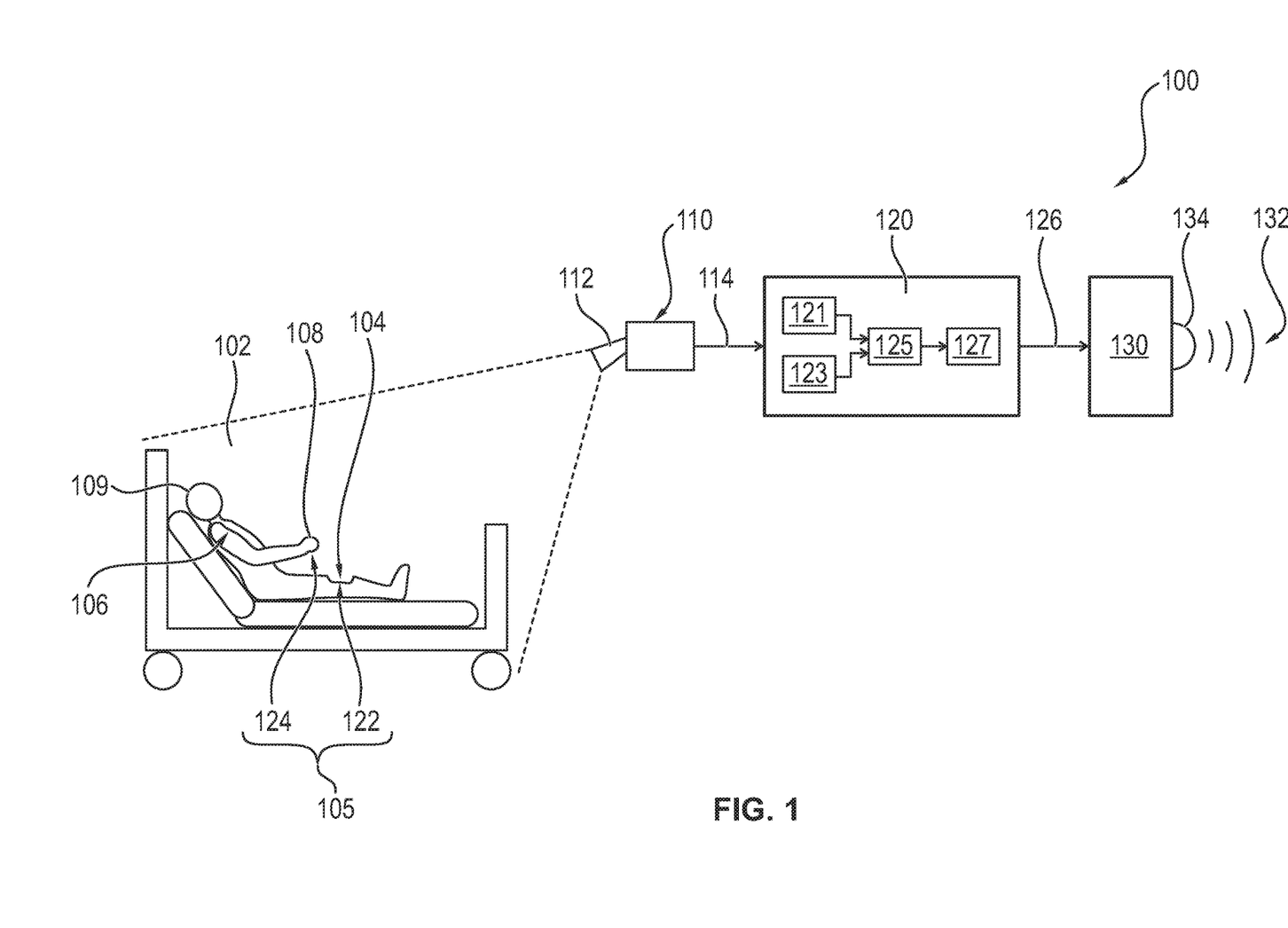
FIG. 1 is a schematic view of a first exemplary embodiment of a system according to the present invention.

Referring to the drawings, FIG. 1 shows a schematic view of a first exemplary embodiment of a system 100 according to the present invention.

The system 100 for the automatic detection of hazardous situations within a monitored area 102 for objects in a medical setting comprises a sensor unit 110, a processor unit 120 and an output unit 130.

The sensor unit 110 has a number of optical sensors 112 and is configured to determine a sensor signal 114 and to output it in real time. Furthermore, the number of optical sensors 112 can in this case be arranged and is configured in the medical setting such that the sensor signal 114 comprises sensor data that indicate a sequence of three-dimensional views of the monitored area 102 during a monitoring time. In the exemplary embodiment shown, the number of optical sensors 112 are installed within a housing, and a three-dimensional view of the monitored area 102 is indicated by the sensor data by the different positions of the optical sensors 112. In one exemplary embodiment, not shown, the at least one sensor of the number of optical sensors is configured to determine the three-dimensional views via a time-of-flight measurement within the monitored area. In another exemplary embodiment, not shown, the at least one sensor of the number of optical sensors is configured to determine the three-dimensional views via a so-called structured-light measurement, i.e., an output of a known radiation pattern in the invisible wavelength range and by a reception of corresponding reflections.

The output of the sensor signal 114 to the processor unit 120 is carried out in the exemplary embodiment shown in a wireless manner via a wireless connection, for example, via WLAN, Bluetooth, BLE or ZigBee. In one exemplary embodiment, not shown, the sensor signal is outputted in a cable-based manner, for example, within the framework of a bus system, especially an Ethernet system.

The processor unit 120 is configured to receive the sensor signal 114 and to carry out an identification of a number of objects 122 to be protected within the monitored area 102 in a first processing step 121 on the basis of the indicated three-dimensional views. Only a wound 104 on the leg of the patient 106 is identified as an object 122 to be protected in this case. This identification was carried out in this case by a gesture-controlled detection of the wound 104 by the processor unit 120. It was detected now by the processor unit 120 in an automated manner that the wound 104 was treated and protected by a dressing (not shown), so that the area of the wound 104 is an object to be protected. In another exemplary embodiment, not shown, an automated detection of the object to be protected is carried out by an analysis of the sensor data such that an object is identified as an object to be protected automatically from the group of predefined objects, which group will be described below, or it is automatically proposed as an object to be protected to a user of the system. This group of predefined objects comprises at least: a person, neck, extremity, infusion, medical device, cable, flexible tube, tube, dressing, and wound.

The processor unit 120 is further configured to carry out an automated detection of hazardous objects 124 within the monitored area 102 in a second processing step 123 on the basis of the indicated three-dimensional views. The hand 108 and the head 109 of the patient 106 are detected as hazardous objects in this case. The monitored area was searched for the automated detection by the processor unit 120 for objects that belong to a predefined group of hazardous objects, which group is stored in a memory of the processor unit 120. This group comprises at least the objects: Foot, bed rail, hand, person, head, animal. In one exemplary embodiment according to the present invention, not shown, the hazardous objects are identified by a manual selection on a user surface of a user interface and are detected thereby by the processor unit.

After the temporary storage of objects 122 to be protected and of hazardous objects 124, the processing unit 120 determines in an assignment step 125 a number of object pairs 105 by an assignment between an object 122 to be protected from the number of objects to be protected and a hazardous object 124. The processor unit 120 detects now that the head 109 of the patient 106 cannot be brought into the vicinity of the wound 104 and it does not therefore represent a risk to the wound 104 as an object to be protected. The processor unit 120 therefore determines the combination of the hand 108 and wound 104 as the only relevant object pair 105 that should therefore be monitored.

Furthermore, the processing unit 120 is configured to monitor the positions of the object 122 to be protected and of the hazardous object 124 of the only object pair 105 being monitored in this exemplary embodiment within the monitored area 102 in the course of the monitoring time within the framework of a monitoring process 127 and to assign a current hazard value to a respective object pair 105 depending on the two current positions and on a group of parameters obtained from an analysis of earlier analysis data. Finally, the respective current hazard values up to the current time are calculated for each object pair 105 over an analysis time interval and a corresponding alarm signal 126 is outputted if a calculated hazard parameter of an object pair 105 exceeds a predefined threshold value. A concrete exemplary embodiment of such a calculation of the hazard values is described within the framework of FIGS. 3 through 5.

In the exemplary embodiment shown, the alarm signal 126 is outputted in a cable-based manner. In one exemplary embodiment, not shown, this output is carried out by a wireless connection, as it is known in different variants in the area of communication technology.

The output unit 130 is configured to receive the alarm signal 126 and to trigger an alarm 132 depending on the alarm signal 126. In the exemplary embodiment shown, the alarm is an acoustic alarm, which is provided by a speaker 134. In an alternative or additional exemplary embodiment, not shown, an optical alarm is triggered by the output unit. In another exemplary embodiment, not shown, logging of the hazardous situation is triggered by the output unit. In another exemplary embodiment, not shown, the alarm is outputted by an external device, which does not belong to the system according to the present invention, but the output unit 130 is configured to trigger the corresponding alarm by a triggering signal at the external device.

In the exemplary embodiment shown, all units of the system 100 according to the present invention have separate housings, because all units are arranged at spaced locations from one another. It is possible, for example, as a result to provide the processor unit at a central location in the medical facility and to operate a number of systems according to the present invention with a corresponding number of different sensor units with a common processor unit.

Figure 2:
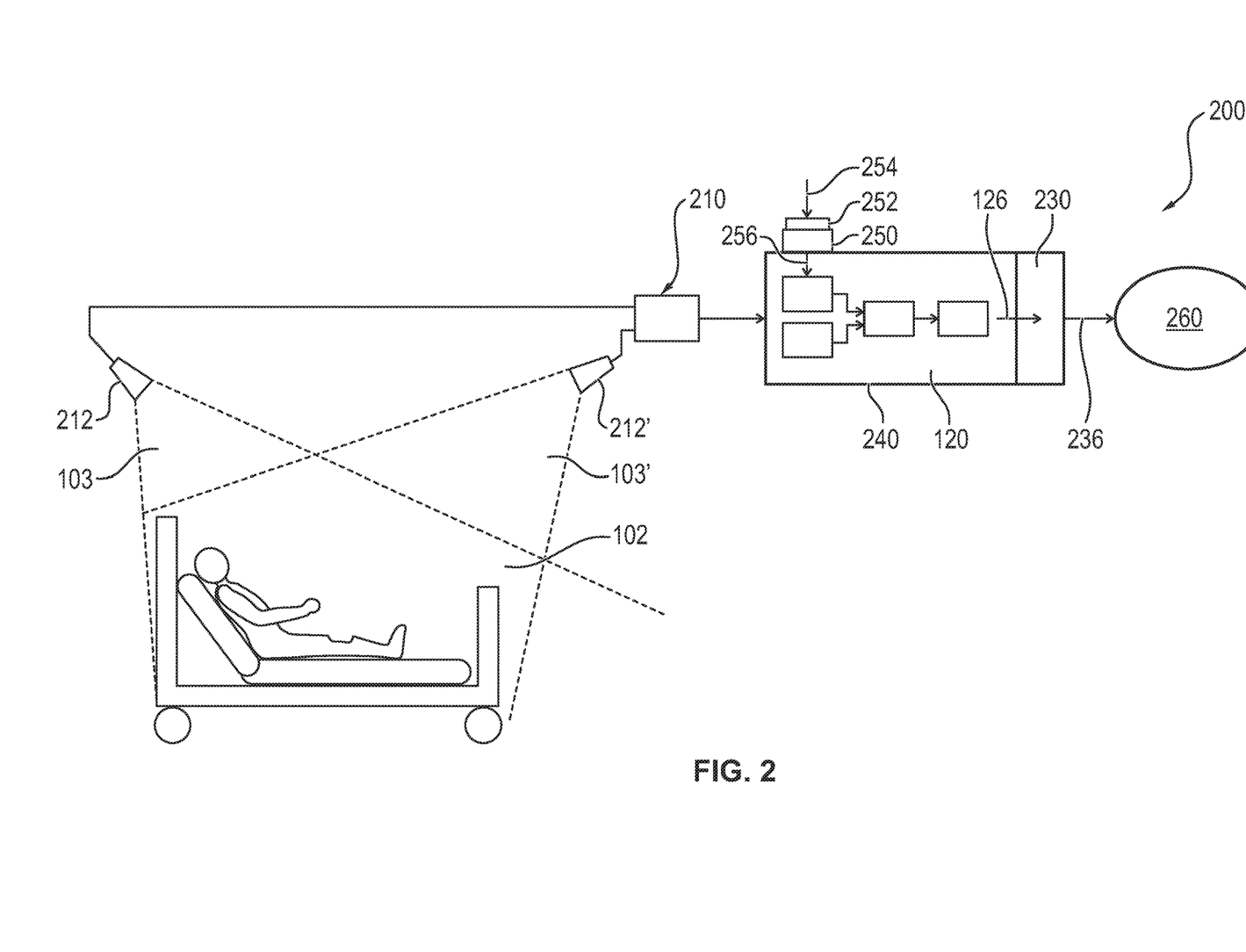
FIG. 2 is a schematic view of a second exemplary embodiment of the system according to the present invention.

FIG. 2 shows a schematic view of a second exemplary embodiment of the system 200 according to the present invention.

The system 200 differs from the system 100 shown in FIG. 1, among other things, in that the sensor unit 210 comprises two separate cameras with a corresponding number of optical sensors 212, 212' and two partial monitored areas 103, 103'. A combined processing of the correspondingly detected sensor data is possible due to the fact that the partial monitored areas 103, 103' have a common monitored area 102 to be monitored as a Jaccard index. As a result, a single sequence of three-dimensional views of this monitored area 102 to be monitored together is indicated.

Furthermore, the system 200 differs from the system 100 from FIG. 1 in that the processor unit 120 and the output unit 230 are arranged in a common housing. The housing 240 comprises, moreover, a user interface 250 as an additional component of the system 200.

The user interface 250 is connected to the processor unit 120 for signal technology. The user interface 250 is configured here to make possible a manual control of the identification of an object to be protected, the detection of a hazardous object and/or of the assignment of the two objects to an object pair. The user interface 250 has for this purpose a touch display 252 for receiving a user input 254. An object to be protected is identified in this case such that the current monitored area 102 is displayed on the touch display 252, and the object to the protected can be identified by touching this object on the touch display 252. The manual detection and storage of a hazardous object are carried out analogously. A manual assignment of two objects to an object pair via the touch display 252 may be carried out, for example, by a swiping gesture of one object over another, by a simultaneous touching of both objects, by tapping two objects on the touch display in rapid succession, and/or by a corresponding note in a data bank of the user interface 250. In one exemplary embodiment, not shown, the user interface is configured as a keyboard, as a computer mouse, as an optical sensor and/or as a joystick. A corresponding input signal 256 is outputted in this case to the processor unit 120 through the user interface 250 corresponding to the user input 254.

In the exemplary embodiment shown, the output unit 230 is connected to the processor unit 120 in a cable-based manner. Unlike in the system 100 from FIG. 1, the output unit 230 is configured to output a triggering signal 236 to a communication network 260 of the hospital corresponding to the alarm signal 126 received and to trigger an alarm within this communication network 260. Both the alarm signal 126 and the correspondingly outputted triggering signal 236 indicate the object to be protected and/or the hazardous object. As a result, an alarm, which is specially adapted to the hazardous situation having developed, can be triggered by the communication network 260. For example, only one alarm generator can be triggered within the hospital room in question, or a group of alarm generators distributed over a hospital ward may be triggered in a serious case, for example, in case of a hazard due to an animal.

Figure 3:
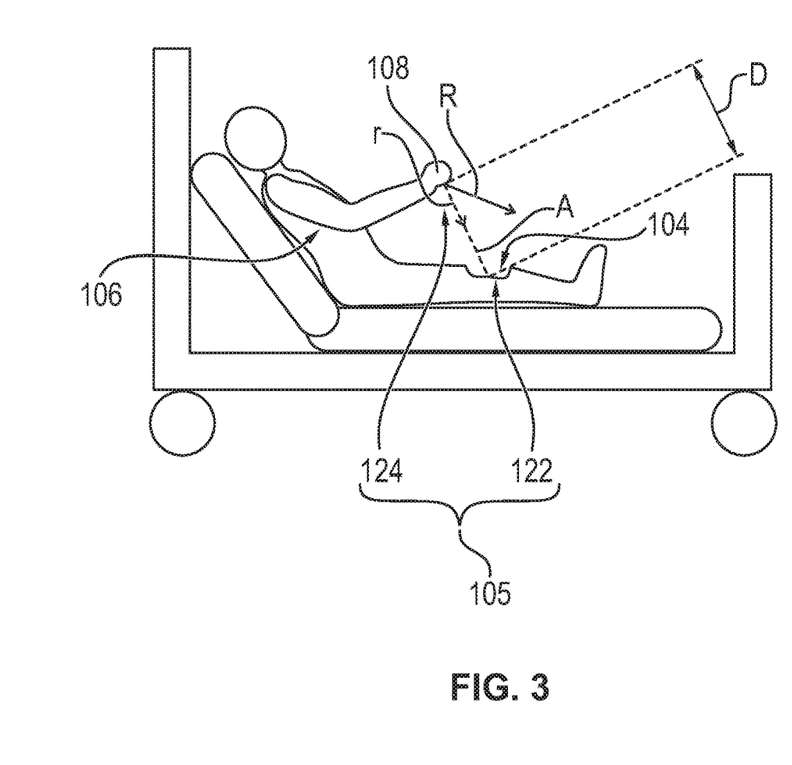
FIG. 3 is a schematic illustration of one of different hazardous situations, wherein the object to be protected and the hazardous object are approaching each other.
Figure 4:
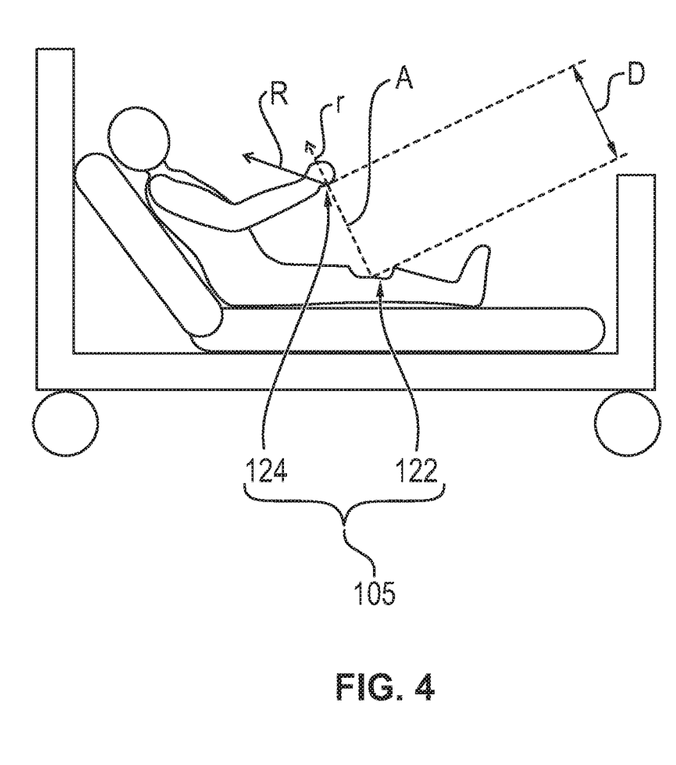
FIG. 4 is a schematic illustration of one of different hazardous situations, wherein the object to be protected and the hazardous object are moving away from one another.
Figure 5:
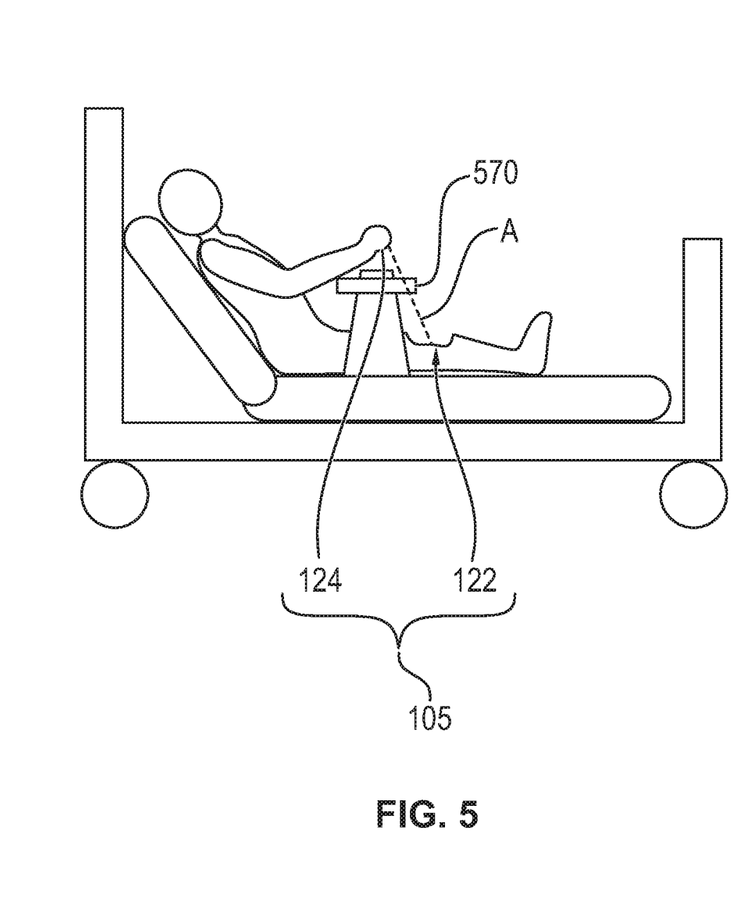
FIG. 5 is a schematic illustration of one of different hazardous situations, wherein an additional object is located between the object to be protected and the hazardous object.

FIGS. 3, 4 and 5 show schematic illustrations of different hazardous situations, wherein the object 122 to be protected and the hazardous object 124 are approaching one another (FIG. 3), wherein the object 122 to be protected and the hazardous object 124 are moving away from one another (FIG. 4), and wherein another object 570 is located between the object 122 to be protected and the hazardous object 124 (FIG. 5).

The assignment of the respective identical object pair 105 to a current hazard value and the calculation of the current hazard values to a hazard parameter shall be explained below according to the preferred exemplary embodiment shown in FIG. 1 on the basis of the hazardous situations shown in FIGS. 3 through 5.

In the three hazardous situations shown, the object 122 to be protected is, as was already explained within the framework of the exemplary embodiments according to FIGS. 1 and 2, a wound 104 on the knee of the patient 106. The hazardous object 124 is again the hand 108 of the patient 106 and the object pair being considered is formed thereby by the wound 104 and by the hand 108 of the patient 106.

The current hazard value $g(t, \vec{x}, p_1, \ldots, p_n)$ assigned to the current time depends on the current time increment t, the current distance vector $\vec{x}$, which has the value of the distance D of the two objects of the object pair and is directed along a direction defined by the current position of the object 122 to be protected and by the current position of the hazardous object 124. Furthermore, the hazard value g is dependent on a plurality of parameters $p_1, \ldots, p_n$, which are obtained from the analysis of earlier analysis data. These parameters are preferably the value D of the current distance vector and/or a current movement direction R of the two objects relative to one another and/or an importance value assigned by the processor unit to the object pair 105 and/or a parameter that shows whether there is a free path between the hazardous object 124 and the object to be protected 122.

The geometric center of this object is used by the processor unit 120 as the current position of the respective object. In one exemplary embodiment, not shown, the distance vector is formed by the point pair of sensor data points of the respective object, which point pair is located closest to one another. The geometric center of the object is not preferably calculated anew with each new data set of sensor data, and this center is especially preferably calculated only once for an object within the monitored area in order to be then maintained at a fixed position relative to a circumference of the object. The calculation time for a processor unit is thus advantageously reduced.

Furthermore, in addition to the distance D, a velocity of the two objects of an object pair 105 relative to one another and a direction R of this movement can be determined as parameters for the hazard values g from the current positions and from a change of these positions over time. In the exemplary embodiment shown, the processor unit 120 analyzes, in addition to the direction of the movement, the percentage r of the movement of the hazardous object in the direction of the object to be protected in the exemplary embodiment shown. This is carried out by a projection of the corresponding movement vector of the direction R to an axis A formed by the two objects.

The percentage r is formed in FIG. 3 such that it points from the hand 108 in the direction of the wound 104. In view to this movement of the two objects of the object pair 105 in relation to one another, the current hazard value g will be greater than the hazard values determined in an earlier step, so that the correspondingly calculated hazard parameter is currently greater than at an earlier time. Should the hazard parameter become greater as a result than the predefined threshold value, the system 100 would output a corresponding alarm signal.

The percentage r is formed in FIG. 4 such that it points from the hand 108 in a direction pointing away from the wound 104. In view to this movement of the two objects of the object pair 105 away from one another, the current hazard value will be lower than the hazard value determined in an earlier step, so that the correspondingly calculated hazard parameter is currently lower than at the earlier time. The triggering of the alarm signal is therefore more unlikely during the movement shown than if the two objects remained in their current positions.

In the exemplary embodiment shown, the calculation of the hazard values is carried out by adding them up for the analysis time interval to the hazard parameter. As a result, the hazard parameter B is obtained by calculation according to $$B(t,T,\vec{x},p_1,\ldots,p_n)=\Sigma_{i=t-T}^{i=t}g(i,\vec{x},p_1,\ldots,p_n).$$

Here, T is the analysis time interval for the object pair being monitored. T indicates here a fixed number of discrete time increments into the past, over which the hazard values g are added up. In another advantageous exemplary embodiment, the hazard parameter B is obtained by calculation according to $$B(t,T,\vec{x},p_1,\ldots,p_n)=\Sigma_{i=Z}^{i=t}g(i,\vec{x},p_1,\ldots,p_n).$$

Here, Z is the time beginning from which an assignment between an objects at risk and an object to be protected has taken place and a corresponding object pair is present for the monitoring.

The hazard value g is preferably a rational number, which is positive if the hazardous object is moving in the direction of the object to be protected, or if a distance between these two objects is currently decreasing more rapidly than in the last time increment, or if an especially high relevance level is assigned to the object to be protected, or if an especially high hazard level is assigned to the hazardous object. The dependence of the hazard value g on the distance may be embodied continuously, for example, by a function rising monotonically with decreasing distance. The hazard value g is zero or negative if a distance between the hazardous object and the object to be protected increases, as this happens in FIG. 4. Furthermore, the hazard value is zero or negative if an object obstructs the direct path between the hazardous object and the object to be protected, as this happens in FIG. 5 due to an object 570 present between the hand 108 and the wound 104, namely, a tablet. A negative hazard value or a hazard value stagnating at zero ensures that the hazard parameter does not become greater, because no positive number is added to the preceding hazard parameter especially in case of calculation by adding up according to this exemplary embodiment.

In a concrete calculation example of the hazardous situation shown in FIG. 3, a hazard value was changed from 0 to 1 after an initial movement of the hand 108 in the direction of the wound 104, so that the hazard parameter also equaled 1. After the hand 108 then remained in one position for some time, the hazard value was again changed to 0 and the hazard parameter remained at 1. The hazard value was changed to 2 with the resuming movement shown, because the distance is also below a corresponding threshold value now in addition to the movement, so that the hazard value is additionally increased hereby by 1, corresponding to the inverse dependence gD=0.5/D beginning from the threshold value 0.5 m with the determined distance D=0.5 m. As a result, the hazard parameter now equals 3. The alarm signal is triggered in this case beginning from the threshold value of the hazard parameter equaling 4.5. This alarm signal is therefore triggered in a next time increment, in which the hand is moving towards the wound, unless a movement away from the wound took place before, which would lead to a negative hazard value and to a corresponding reduction of the hazard parameter.

The hazard value is preferably a linear function of the importance value, which is assigned to the respective object pair by the processor unit. The importance value is preferably proportionally dependent on the predefined relevance level of the object to be protected and/or on the predefined hazard level of the hazardous object.

The identification of concrete rational numbers for the hazard level and/or for the relevance level and/or for the importance level and/or for the hazard level is carried out in a preferred exemplary embodiment by a manual user input and/or by a predefined, user-provided assignment of values, which is stored in a memory of the processor unit. Individual preferences can hereby be taken into consideration when assessing a hazardous situation.

Figure 6:
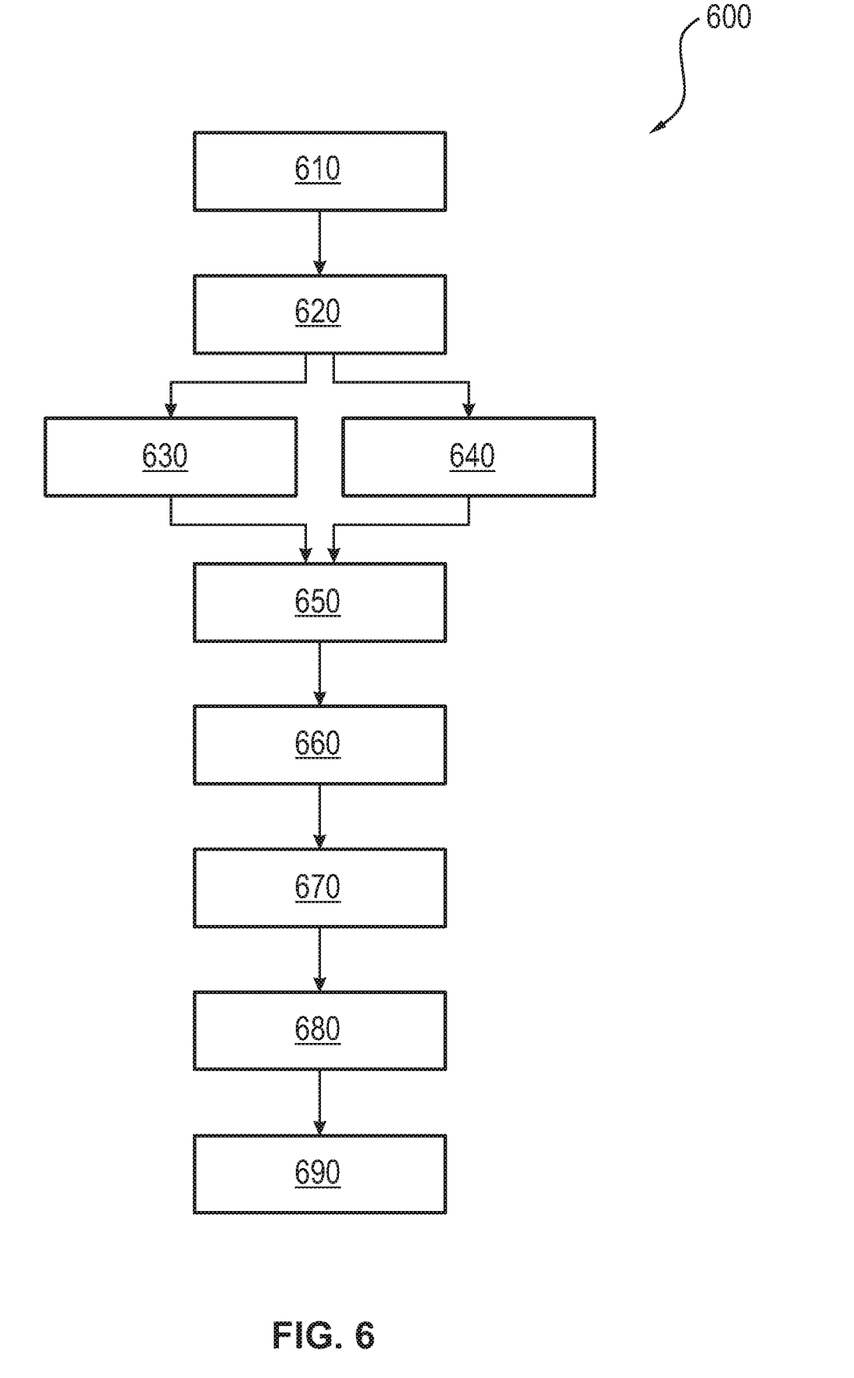
FIG. 6 is a flow chart of a first exemplary embodiment of a process according to the present invention.

FIG. 6 shows a flow chart of a first exemplary embodiment of a process 600 according to the present invention.

The process 600 for the automatic detection of hazardous situations within a monitored area for objects in the medical setting has a sequence of the steps described below:

A first step 610 comprises the determination of a sensor signal, which comprises sensor data, which indicate a sequence of three-dimensional views of the monitored area over a monitoring time, and the outputting of the sensor signal in real time.

A next step 620 comprises the reception of the sensor signal.

A next step 630 comprises the identification of a number of objects to be protected within the monitored area on the basis of the indicated three-dimensional views.

A step 640, which can be carried out simultaneously with step 630, comprises the detection, especially an automated detection of hazardous objects within the monitored area on the basis of the indicated three-dimensional views.

Another step 650 comprises the determination of a number of object pairs by an assignment between an object to be protected from the number of objects to be protected and a hazardous object.

A next step 660 comprises the assignment of a current hazard value to a respective object pair as a function of the current positions of the object to be protected and of the hazardous object and of a group of parameters obtained from an analysis of earlier analysis data.

A next step 670 comprises the calculation of the current hazard values for a respective object pair into a respective hazard parameter over an analysis time interval up to the current time.

Another step 680 comprises the outputting of a corresponding alarm signal if the hazard parameter thus determined exceeds a predefined threshold value.

A final step 690 comprises the reception of the alarm signal and the triggering of an alarm as a function of the alarm signal.

Steps 610 and 620 are typically carried out in real time, i.e., in time increments following one another at short intervals.

Steps 630 and 640 may be carried out simultaneously with one another or one following another in any desired sequence.

Step 650 is carried out once during the monitoring of an object pair, whereas steps 660 and 670 describe the monitoring process proper and are carried out repeatedly in consecutive time increments, so that the respective hazard parameter is always calculated with the hazard value adapted to the current situation in the monitored area. Steps 680 and 690 are carried out preferably only once one after another within the framework of the monitoring of an object pair, namely, after the predefined threshold value is exceeded by the hazard parameter.

In a preferred exemplary embodiment, the calculation of the current hazard values corresponding to step 670 is carried out by adding up these hazard values over the analysis time interval up to the current time.

The process according to the present invention preferably comprises in an additional step a deactivation of the process 600 if the processor unit detects by means of the sensor signal the presence of medical staff within the monitored area. In a preferred example of this variant, the process 600 is continued with the data detected prior to the deactivation due to the medical staff if the detected medical staff has left the monitored area. In a variant of this embodiment, the medical staff is distinguished from other persons by an automatic detection of an identification number carried by the medical staff. This is possible, for example, by means of a key card carried along, on which the identification number is stored, and/or by a corresponding arrangement of an identification information on the clothing of the medical staff. In an alternative or additional example, the identification information is provided manually by the medical staff.

While specific embodiments of the invention have been shown and described in detail to illustrate the application of the principles of the invention, it will be understood that the invention may be embodied otherwise without departing from such principles.

LIST OF REFERENCE NUMBERS 100, 200 System
102 Monitored area
103, 103' Partial monitored areas
104 Wound
105 Object pair
106 Patient
108 Hand
109 Head
110, 210 Sensor unit
112, 212, 212' Number of optical sensors
114 Sensor signal
120 Processor unit
121 First processing step
122 Object to be protected
123 Second processing step
124 Hazardous object
125 Assignment step
126 Alarm signal
127 Monitoring process
130, 230 Output unit
132 Alarm
134 Speaker
236 Triggering signal
240 Housing
250 User interface
252 Touch display
254 User input
256 Input signal
260 Communication network
570 Additional object
600 Process
610, 620, 630, 640, Process steps
650, 660, 670, 680,
690
D Distance between objects being monitored
R Movement direction
r Percentage of movement
A Axis between monitored objects

What is claimed is:
1. A system for the automatic detection of hazardous situations within a monitored area for objects in a medical setting, the system comprising:
a sensor unit with a plurality of optical sensors, the sensor unit being configured to determine a sensor signal and to output same in real time, wherein the plurality of optical sensors are arrangeable in the medical setting and configured such that the sensor signal comprises sensor data, which indicate a sequence of three-dimensional views of the monitored area over a monitoring time;
a processor unit configured to receive the sensor signal, and configured to:
carry out an identification of a number of objects to be protected within the monitored area based on the indicated three-dimensional views;
carry out a detection of hazardous objects within the monitored area based on the indicated three-dimensional views and to determine a number of object pairs by an assignment between an object to be protected from the number of objects to be protected and a hazardous object;
monitor positions of the object to be protected and the hazardous object of a respective object pair within the monitored area and assign a current hazard value to a respective object pair as a function of two current positions and of a group of parameters obtained from an analysis of earlier analysis data; and
calculate respective current hazard values up to a current time over an analysis time interval for each object pair to determine a respective hazard parameter over an analysis time interval up to the current time and output a corresponding alarm signal if the hazard parameter of an object pair exceeds a predefined threshold value, and
an output unit configured to receive the alarm signal and to trigger an alarm as a function of the alarm signal, wherein:
an importance value, which is obtained from a predefined relevance level of the object to be protected and/or from a predefined hazard level of the hazardous object, is assigned to each object pair by the processor unit; and
a current hazard level of the object pair depends on the importance value.

2. A system in accordance with claim 1, wherein the assignment between an object to be protected and a hazardous object depends on a current position of the hazardous object within the monitored area relative to the object to be protected.

3. A system in accordance with claim 1, wherein the parameters obtained from the analysis of the earlier analysis data comprise a distance between the objects of an object pair and a direction of a movement of the objects of an object pair relative to one another.

4. A system for the automatic detection of hazardous situations within a monitored area for objects in a medical setting, the system comprising:
a sensor unit with a plurality of optical sensors, the sensor unit being configured to determine a sensor signal and to output same in real time, wherein the plurality of optical sensors are arrangeable in the medical setting and configured such that the sensor signal comprises sensor data, which indicate a sequence of three-dimensional views of the monitored area over a monitoring time;
a processor unit configured to receive the sensor signal, and configured to:
carry out an identification of a number of objects to be protected within the monitored area based on the indicated three-dimensional views;
carry out a detection of hazardous objects within the monitored area based on the indicated three-dimensional views and to determine a number of object pairs by an assignment between an object to be protected from the number of objects to be protected and a hazardous object;
monitor positions of the object to be protected and the hazardous object of a respective object pair within the monitored area and assign a current hazard value to a respective object pair as a function of two current positions and of a group of parameters obtained from an analysis of earlier analysis data; and
calculate respective current hazard values up to a current time over an analysis time interval for each object pair to determine a respective hazard parameter over an analysis time interval up to the current time and output a corresponding alarm signal if the hazard parameter of an object pair exceeds a predefined threshold value, and
an output unit configured to receive the alarm signal and to trigger an alarm as a function of the alarm signal, wherein the current hazard value of an object pair also depends on whether a direct path between the object to be protected and the hazardous object is obstructed by an additional object.

5. A system in accordance with claim 1, wherein the identification of the number of objects to be protected and/or the detection of hazardous objects is carried out by an automated object detection.

6. A system in accordance with claim 1, wherein the identification of the number of objects to be protected is carried out at least partially by an interaction with a user of the system.

7. A system in accordance with claim 1, wherein the analysis time interval is the time interval that is formed by a determination time for the determination of the corresponding object pair and the current time.

8. A system in accordance with claim 1, further comprising a user interface connected to the processor unit and configured to provide a manual control of the identification of an object to be protected, of the detection of a hazardous object and/or of the assignment of the two objects to an object pair.

9. A system in accordance with claim 1, wherein the object to be protected is at least one object from the group comprising a person, neck, extremity, infusion, medical device, cable, flexible tube, tube, dressing, and wound.

10. A system in accordance with claim 1, wherein the hazardous object is at least one object from the group comprising a hand, foot, person, head, animal, and bed rail.

11. A system in accordance with claim 1, wherein the alarm signal indicates the object to be protected and/or the hazardous object.

12. A process for an automatic detection of hazardous situations within a monitored area for objects in a medical setting, the process comprising the steps of:
determining a sensor signal, which comprises sensor data, which indicate a sequence of three-dimensional views of the monitored area over a monitoring time, and outputting the sensor signal in real time;
receiving the sensor signal;
identifying a number of objects to be protected within the monitored area based on the indicated three-dimensional views;
detecting hazardous objects within the monitored area based on the indicated three-dimensional views;
determining a number of object pairs by an assignment between an object to the protected from the number of objects to be protected and a hazardous object;

assigning a current hazard value to a respective object pair as a function of the current positions of the object to be protected and the hazardous object and of a group of parameters obtained from an analysis of earlier analysis data;

calculating the current hazard values for a respective object pair to determine a respective hazard parameter over an analysis time interval up to the current time;

outputting of a corresponding alarm signal if the hazard parameter thus determined exceeds a predefined threshold value; and receive the alarm signal and trigger an alarm as a function of the alarm signal, wherein the calculation of the current hazard values comprises the adding up of current hazard values up to the current time to obtain the respective hazard parameter of the object pair.

13. A process according to claim 12, further comprising providing a program with a program code for carrying out the process when the program code is run on a computer, on a processor or on a programmable hardware component.

14. A system for the automatic detection of hazardous situations within a monitored area for objects in a medical setting, the system comprising:

a sensor unit with a plurality of optical sensors, the sensor unit being configured to determine a sensor signal and to output same in real time, wherein the plurality of optical sensors are arrangeable in the medical setting and configured such that the sensor signal comprises sensor data, which indicate a sequence of three-dimensional views of the monitored area over a monitoring time;

a processor unit configured to receive the sensor signal, and configured to:

carry out an identification of a number of objects to be protected within the monitored area based on the indicated three-dimensional views;

carry out a detection of hazardous objects within the monitored area based on the indicated three-dimensional views and to determine a number of object pairs by an assignment between an object to be protected from the number of objects to be protected and a hazardous object;

monitor positions of the object to be protected and the hazardous object of a respective object pair within the monitored area and assign a current hazard value to a respective object pair as a function of two current positions and of a group of parameters obtained from an analysis of earlier analysis data; and calculate respective current hazard values up to a current time over an analysis time interval for each object pair to determine a respective hazard parameter over an analysis time interval up to the current time and output a corresponding alarm signal if the hazard parameter of an object pair exceeds a predefined threshold value, and an output unit configured to receive the alarm signal and to trigger an alarm as a function of the alarm signal, wherein the calculation of the current hazard values comprises the adding up of current hazard values up to the current time to obtain the respective hazard parameter of the object pair.

15. A system in accordance with claim 14, wherein the assignment between an object to be protected and a hazardous object depends on a current position of the hazardous object within the monitored area relative to the object to be protected.

16. A system in accordance with claim 14, wherein the parameters obtained from the analysis of the earlier analysis data comprise a distance between the objects of an object pair and a direction of a movement of the objects of an object pair relative to one another.

17. A system in accordance with claim 14, wherein the identification of the number of objects to be protected and/or the detection of hazardous objects is carried out by an automated object detection.

18. A system in accordance with claim 14, wherein the identification of the number of objects to be protected is carried out at least partially by an interaction with a user of the system.

19. A system in accordance with claim 14, wherein the analysis time interval is the time interval that is formed by a determination time for the determination of the corresponding object pair and the current time.

20. A system in accordance with claim 14, further comprising a user interface connected to the processor unit and configured to provide a manual control of the identification of an object to be protected, of the detection of a hazardous object and/or of the assignment of the two objects to an object pair.

* * * * *